United States Patent [19]
Larson

[11] 3,966,310
[45] June 29, 1976

[54] PUPILLOMETER AND METHOD OF USE THEREOF

[76] Inventor: Merlin D. Larson, 3420 21st St., San Francisco, Calif. 94110

[22] Filed: Feb. 15, 1974

[21] Appl. No.: 442,760

[52] U.S. Cl. ................................................ 351/16
[51] Int. Cl.[2] ...................................... A61B 3/10
[58] Field of Search .............. 351/1, 6, 39, 16, 5, 351/36; 350/235; 240/2 M, 2.18, 81 A; 355/70

[56] References Cited
UNITED STATES PATENTS

| | | | |
|---|---|---|---|
| 2,326,030 | 8/1943 | Hearn | 351/5 |
| 2,682,816 | 7/1954 | Walden | 355/70 X |
| 2,965,751 | 12/1960 | Stiffel | 240/81 A X |
| 3,165,025 | 1/1965 | Hart | 355/70 X |

FOREIGN PATENTS OR APPLICATIONS 463,778 4/1937 United Kingdom ................. 350/235

OTHER PUBLICATIONS

Holladay, J. Opt. Soc. Am. & Review Sci. Inst., "The Fund . . . Visibility," vol. 12, No. 4, Apr. 1926, pp. 271–319.

Kanofsky, Amer. J. Ophthalm, "Simplified . . . Pupillometry," vol. 51, No. 6, pp. 1273–1276, June 1961.

J. W. Walker et al., The Optician, "An Attempt . . . Reflex," vol. 150, No. 3875, July 9, 1965, pp. 8–11.

Primary Examiner—Paul A. Sacher
Attorney, Agent, or Firm—Phillips, Moore, Weissenberger Lempio & Strabala

[57] ABSTRACT

Apparatus for observing reaction of the pupil of an eye includes a first light source for generally illuminating the eye, and a second light source which may be selectively actuated to direct light to the eye in the area of the pupil. The reaction of the pupil to this application of light from the second light source is observed through a lens which is included as part of the apparatus.

2 Claims, 7 Drawing Figures

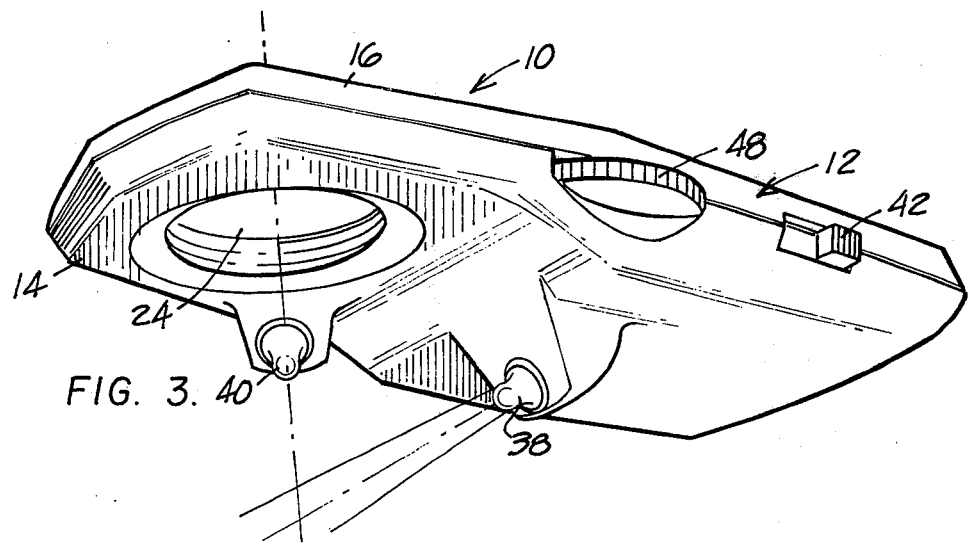
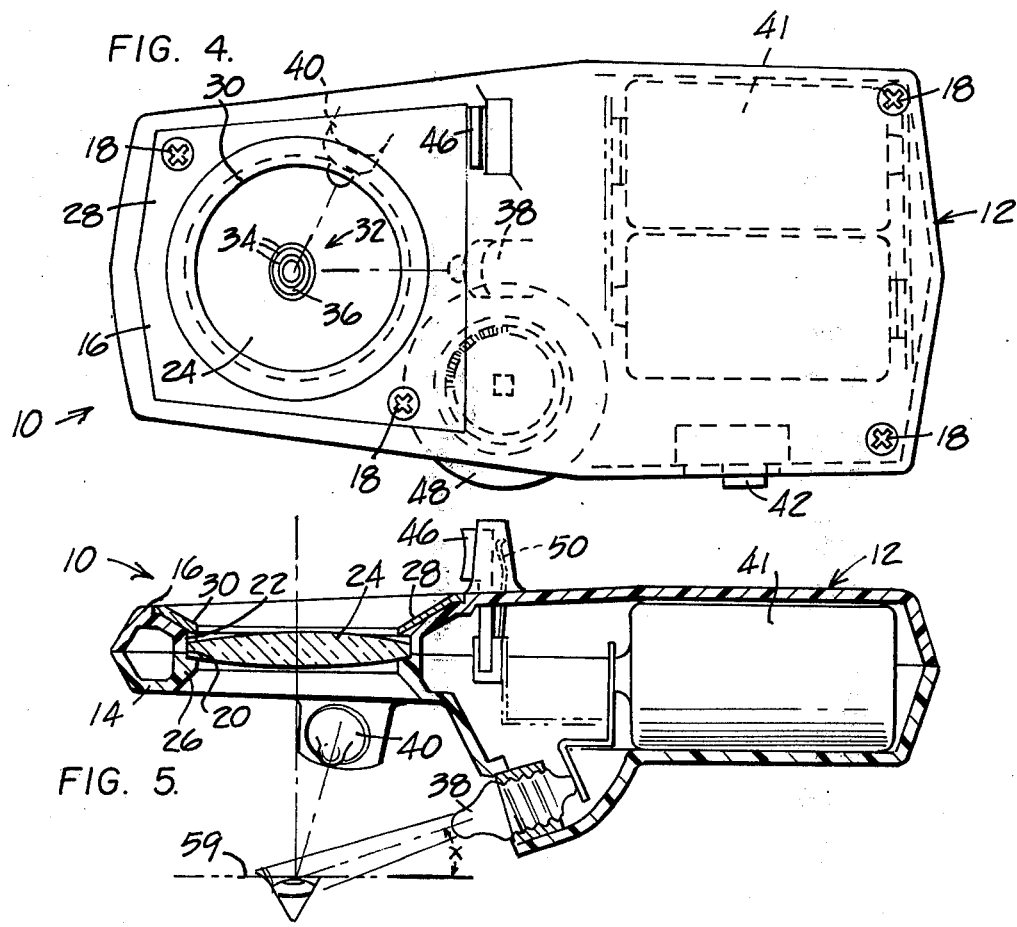

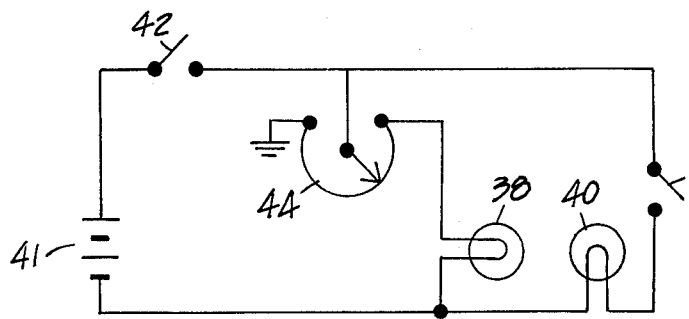
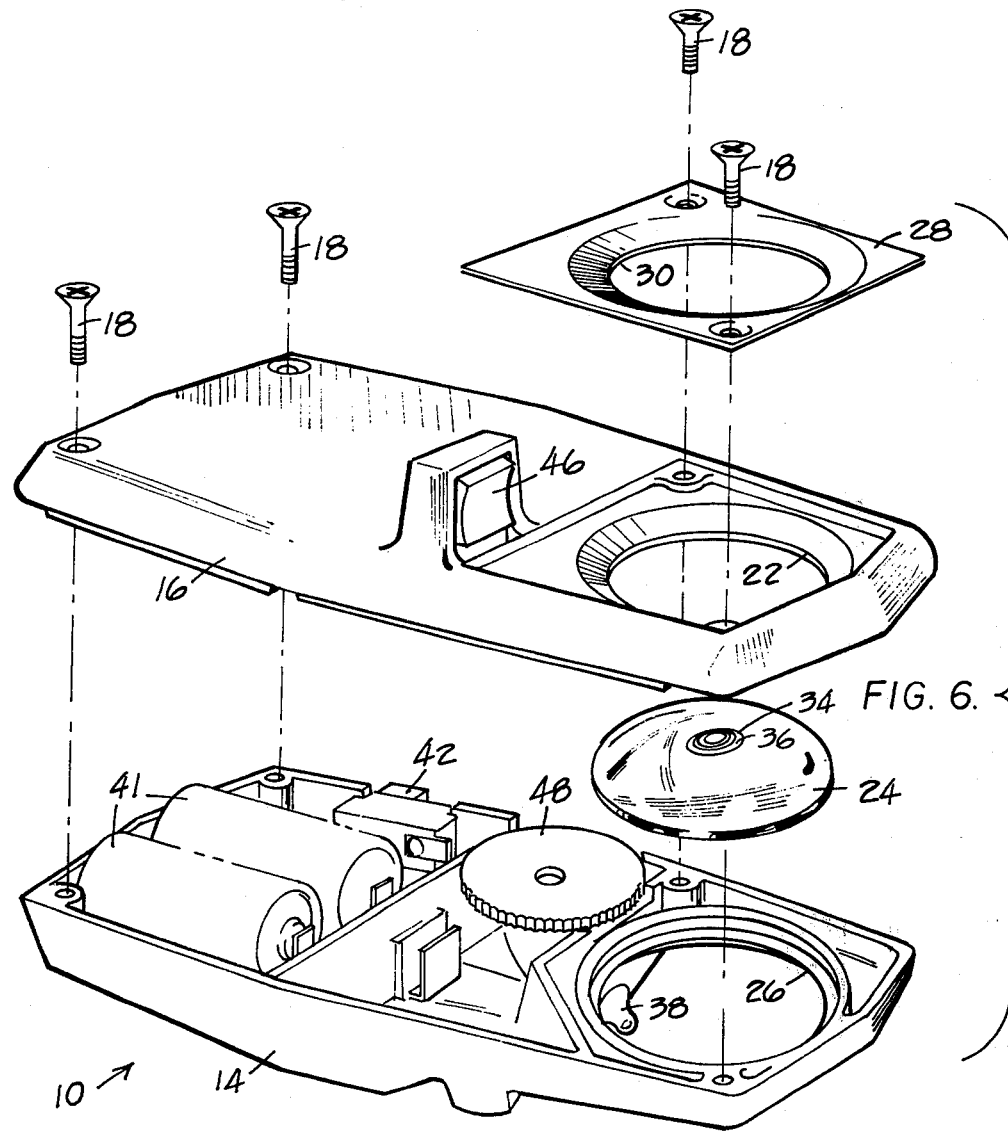

PUPILLOMETER AND METHOD OF USE THEREOF

BACKGROUND OF THE INVENTION

This invention relates to pupillometry, and more particularly, to a system which includes means for inducing a reaction in the iris and pupil of an eye and observing such reaction.

Observation of the size of the pupil of an eye, determined by the state of the iris thereof under generally steady-illumination conditions, and also the reaction of the iris and pupil upon application of light thereto, can provide valuable information for determining the physical state of the person involved. For example, if the person is being anesthetized in preparation for, for example, an operation, the observation of the reflex of the iris upon application of light thereto can be extremely valuable in determining the extent to which the anesthetic is affecting the patient. That is, if there is little or no reaction of the iris to a relatively sudden application of light, the patient can be assumed to be further anesthetized than if such reaction is relatively great or brisk.

Additionally, measurement of the absolute size of the pupil of the eye may provide valuable information. For example, it is well known that the pupils of a person who is under the effect of certain drugs, such as morphine, are reduced in size. With certain other drugs, the pupils may be enlarged. Thus, the observation of size of the pupil and the reaction of the iris and pupil to a relatively sudden application of light, can provide very valuable information toward determining the physical state of the person involved.

Systems which are generally related to the problem involved above are disclosed in U.S. Pat. No. 2,303,221 to Moy, U.S. Pat. No. 2,573,464 to Lowenstein et al, U.S. Pat. No. 3,533,683 to Stark et al, U.S. Pat. No. 3,533,684 to Stark et al, and U.S. Pat. No. 3,535,026 to Coss. It is to be noted that, while such systems have been found relatively effective in the uses for which they were designed, certain of these systems are relatively complicated in construction (U.S. Pat. Nos. 2,573,464, 3,533,683 and 3,533,684). Furthermore, the devices of U.S. Pat. Nos. 2,303,221 and 3,535,026 include means which allow the measurement of the size of the pupil, but provide no means for properly allowing observation of the reaction or reflex of the iris and pupil of the eye to application of light thereto.

Other known devices used along these lines are a template defining a plurality of holes, one of which is lined up with the pupil for measuring the size thereof, a ruler with which the pupil is measured, and a photographing system which takes a photo of the eye, from which photograph the pupil size can be measured.

Of general interest in this area are U.S. Pat. No. 1,918,540 to Hartinger, and U.S. Pat. No. 3,012,462 to Kosche et al.

SUMMARY OF THE INVENTION

It is an object of this invention to provide apparatus for observing reaction of the iris and pupil of an eye upon application of light thereto.

It is a further object of this invention to provide apparatus which, while fulfilling the above object, includes means for measuring the absolute size of the pupil of an eye.

It is a still further object of this invention to provide apparatus which, while fulfilling the above objects, is extremely convenient in use, and may be operated and controlled by one hand of the user thereof.

It is a still further object of this invention to provide apparatus which, while fulfilling the above objects, is extremely simple in design and construction.

Broadly stated, the pupillometer of the present invention is for observing the reaction of the iris and pupil of an eye, and comprises a body, and a first light source mounted relative to said body for emitting light, said first light source being positioned so that said light emitted thereby illuminates the eye in the area of the pupil. A second light source is mounted relative to the body for emitting light, said second light source being positioned so that light emitted thereby travels more directly into the pupil than the light emitted from said first light source. Means are included for selectively actuating the second light source, so that reaction of the iris and pupil to the light emitted from the second light source may be observed. Broadly stated, the invention further comprises a method of applying light to an eye in the area of the iris and pupil thereof for observing the reaction of the iris and pupil thereof. Such method comprises the steps of illuminating the eye in the area of the iris and pupil from a first light source, and selectively directing light from a second light source to the area of the iris and pupil.

BRIEF DESCRIPTION OF THE DRAWINGS

These and other objects of the invention will become apparent from a study of the following specification and drawings, in which:

FIG. 3 is a perspective view of the apparatus, showing the particular arrangement of the light sources thereof;

FIG. 4 is a plan view of the apparatus;

FIG. 5 is a sectional elevation of the apparatus;

FIG. 6 is an exploded perspective view of the apparatus; and

FIG. 7 is a schematic illustration of the circuitry of the apparatus for actuating the light sources thereof.

DESCRIPTION OF THE PREFERRED EMBODIMENT

Figure 2:
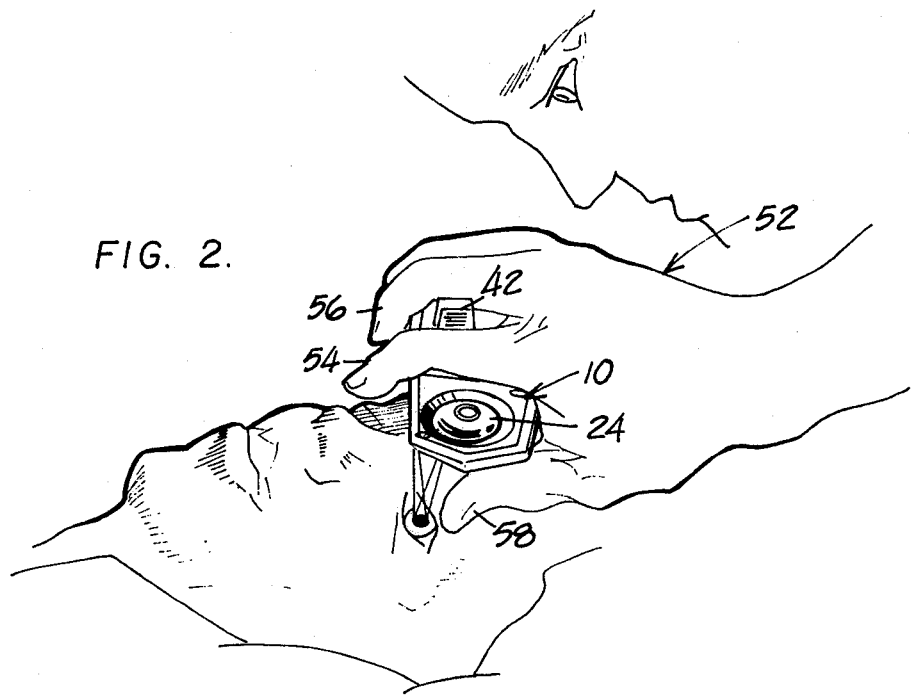
FIG. 2 is an overall perspective view showing the use of the apparatus.
Figure 1:
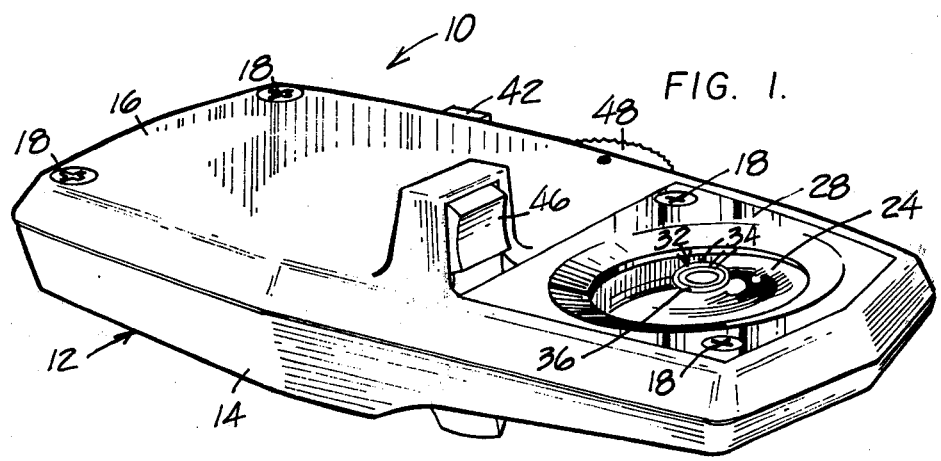
FIG. 1 is a perspective view of the inventive apparatus.

Shown in FIGS. 1-6 is the pupillometer apparatus 10 which is the subject of this application. Such apparatus 10 includes a body 12 made up of body portions 14,16 secured together by screws 18. The body portions 14,16 define apertures 20,22 which are in registry when such portions 14,16 are fitted together. A magnifying lens 24 is disposed within the apertures 20,22 (FIG. 5), and the outer edge thereof is seated on an annular shoulder 26 defined by the body portion 14. A retainer 28 defines an inner annular edge 30 which seats on and about the outer edge of the lens 24, the retainer 28 being removably held in place by a pair of the screws 18, as shown, whereby the lens 24 is removably mounted relative to the body 12. A plurality of markings 32 are positioned on the surface of the lens 24, such markings 32 in this case being a plurality of oval markings 34 on a decal 36 or the like disposed on the surface of the lens 24.

The body portion 14 has mounted thereon as shown a light bulb 38, and a light bulb 40. Batteries 41 mounted within the body 12 are utilized as the power source for actuating these bulbs 38,40, through circuitry as shown schematically in FIG. 7. As shown therein, a master switch 42 (mounted on body 12) may be closed to supply power through a rheostat 44 to the bulb 38. The closing of switch 42 also supplies power to a second switch 46, the closing of which in turn supplies power to the bulb 40. Rheostat 44 is used to vary resistance thereof in the conventional manner through dial 48 associated with body 12, to in turn vary the intensity of the light emitted from bulb 38. Switch 46 may be selectively closed against the resilience of a spring 50 associated therewith, so that the bulb 40 directs light therefrom. Each bulb is of the well known type which emits a beam of light which diverges somewhat therefrom, but which extends generally along a straight line therefrom (generally unidirectional), as best shown in FIGS. 3 and 5. However, the beam of light from bulb 38 is of greater divergence (i.e., greater "spray") than the beam of light from bulb 40. The bulbs 38,40 are positioned relative to body 12 so that the light beams therefrom are in converging and intersecting relation.

In using the apparatus 10, it is to be noted that the body 12 is held in the hand 52 of the user or observer, the body 12 being properly sized to be so held. The switch 46 for actuating the bulb 40 is positioned so that with the body 12 so held, such switch 46 is disposed between the adjacent index and middle fingers 54,56 of the hand 52. After switch 42 has been closed, pressure applied to the switch 46 by movement of the index finger 54 in the direction of the middle finger 56 actuates bulb 40. Thus, convenient means are provided for selectively actuating the bulb 40, with control over the hand-held apparatus 10 being maintained.

The user of the apparatus 10 then sets the rheostat 44 by means of dial 48 to illuminate the bulb 38 to a level necessary to illuminate the area of the iris and pupil of the eye. The observer uses his thumb 58 as shown in FIG. 2 to contact and hold up the eyelid, to expose such area of the eye, and the lens 28 and bulbs 38,40 are positioned and angled for proper functioning with the thumb 58 substantially fully extended.

In such operating position of the apparatus 10, the user observes the eye through the lens 28, and the beam of light from the bulb 38 is positioned to be directed substantially across or laterally of the pupil, so that such light has little effect on the action of the iris. In fact, the beam of light from bulb 38 may with great advantage be directed generally along a line within the limits of from 0° to 20° from a plane 59 which is in tangential relation with the center of the pupil (FIG. 5) such angle being indicated at X. In addition, the bulb 40 is positioned so that the beam of light emitted therefrom is applied more directly into the pupil and iris than the beam of light from bulb 38, so that the iris is relatively highly exposed thereto.

With the apparatus 10 so positioned and ready for further use, the iris and pupil are observed by means of the light from bulb 38. The bulb 40 is then actuated by movement of the index finger 54 toward the middle finger 56, closing switch 46. Light is thereby directed from bulb 40 to the eye in the area of the pupil and iris, so that reaction of the iris and pupil to the relatively sudden application of light thereto from the bulb 40 may be observed through lens 28.

The observation of reflex action of the iris (and pupil) can then be used to aid in determining the physical state of the person whose eye is being observed, as previously described.

The oval markings 32 are positioned one within the other, to allow use of the apparatus when the pupil is viewed obliquely, and not from directly above.

Such markings 32 positioned on the lens 28 are sized in relation to the power of the lens 28 and the distance of the pupil therefrom to indicate the absolute size of the pupil being observed, such information being useful in accordance with the earlier discussion.

It will be understood that the lens 28 may be removed, and another substituted therefor, if advantageous in the particular use of the device.

The apparatus 10 is particularly suitable for observing the reactions of small (miotic) pupils, which are often seen in patients who are under the influence of anesthetic drugs.

What is claimed is:
1. Hand-operable apparatus for observing reaction of the iris in the pupil of an eye, comprising:
 a body sized to be hand-held;
 a plurality of generally unidirectional light sources mounted on said body and positioned to direct light therefrom to said eye in the area of said pupil upon hand-positioning of said body, at least one light source emitting only a first generally straight light beam impinging on said eye generally along a line within the limits of from 0° to 20° from a plane tangent to the center of the pupil, and at least one other generally unidirectional light source of said plurality of light sources emitting only a second generally straight light beam impinging on said eye in the vicinity of said pupil more directly into said pupil and iris than said light means impinging on said eye within said 0° to 20° limits, said light beam impinging within said 0° to 20° limits being of greater divergence than said more directly impinging light beam;
 means for selectively actuating the light source impinging more directly on the pupil;
 lens means mounted on said body and positioned for allowing observation therethrough of the reaction of the iris and pupil to the selectively actuated light source impinging more directly on the pupil;
 marking means mounted on said lens means and sized in relation to said lens means and the distance of the pupil therefrom to indicate the size of the pupil being observed;
 said means for selectively actuating the light source comprising pressure-sensitive switch means mounted on said body and positioned between adjacent fingers of the hand with the body so hand-held, said pressure-sensitive switch means actuating said light source upon application of pressure applied thereto by one adjacent finger in the direction of the other adjacent finger.
2. An apparatus as in claim 1, further comprising means for selectively varying the intensity of the light source emitting the beam impinging on the eye within said 0° to 20° limits.

* * * * *